United States Patent [19]

Bredow et al.

[11] Patent Number: 5,154,335
[45] Date of Patent: Oct. 13, 1992

[54] REFILLABLE DISPENSER FOR MOIST ADHESIVE ELECTRODES

[75] Inventors: Timothy S. Bredow; David L. Robbins, both of St. Paul, Minn.

[73] Assignee: Minnesota Mining and Manufacturing Company, St. Paul, Minn.

[21] Appl. No.: 583,175

[22] Filed: Sep. 14, 1990

[51] Int. Cl.⁵ .................................. B26F 3/02
[52] U.S. Cl. ............................. 225/40; 225/56; 225/90
[58] Field of Search ................ 225/40, 43, 47, 48, 225/49, 50, 53, 54, 56, 57, 58, 90

[56] References Cited

U.S. PATENT DOCUMENTS

| | | | |
|---|---|---|---|
| 1,026,778 | 5/1912 | Toles | 225/43 |
| 2,253,744 | 8/1941 | Witt | 225/43 |
| 2,600,904 | 6/1952 | Morgan | 225/47 |
| 2,622,815 | 12/1952 | Waterman | 225/47 |
| 3,227,341 | 1/1966 | Costello | 225/54 |
| 3,530,494 | 9/1970 | Baratta | 206/63.2 |
| 4,339,035 | 7/1982 | Marcus et al. | 206/370 |
| 4,462,507 | 7/1984 | Margulies | 221/63 |
| 4,566,606 | 1/1986 | Kling | 221/25 |
| 4,574,979 | 3/1986 | Hackett | 221/73 |
| 4,576,311 | 3/1986 | Horton et al. | 221/73 |
| 4,584,962 | 4/1986 | Cartmell | 118/43 |
| 4,606,134 | 8/1986 | Flick | 33/414 |
| 4,821,918 | 4/1989 | Turner | 221/70 |
| 4,830,305 | 5/1989 | Guggi et al. | 242/71.7 |
| 4,848,353 | 7/1989 | Engel | 128/640 |
| 5,065,925 | 11/1991 | Ridenour | 225/78 |

OTHER PUBLICATIONS

Berlant, "Method of Determining Optimal Stimulation Sites for Transcutaneous Electrical Nerve Stimulation", *Physical Therapy*, vol. 64, Jun. 1984, pp. 924-928.
Snyder-Mackler et al., "Clinical Electrophysilogy", Williams & Wilkins, pp. 30-33.
Mannheimer, "Electrode Placements for Transcutaneous Electrical Nerve Stimulation", *Physical Therapy* Volume 58, Dec. 1978, pp. 1455-1462.

*Primary Examiner*—P. W. Echols
*Assistant Examiner*—John M. Husar
*Attorney, Agent, or Firm*—Gary L. Griswold; Walter N. Kirn; Jeffrey J. Hohenshell

[57] ABSTRACT

The present invention provides in combination, a supply roll comprising an elongate liner, a multiplicity of electrodes, and a coating of moist adhesive on the electrodes that releasably adheres the electrodes in spaced relationship along the liner, and a refillable air-restricting dispenser comprising a plurality of walls forming a housing. The walls comprise a hollow tubular peripheral wall, and first and second opposite end walls, and define a central cavity within the housing. The peripheral wall has a slot communicating between inner and outer surfaces of the peripheral wall. The slot is adapted to afford passage of the liner with electrodes adhered thereto. A shield is present which covers the slot, and an element mounts the shield on the housing for movement between an open position spaced from at least a portion of the slot to afford withdrawing the end portion of the liner with the electrodes adhered thereto through the slot, and a closed position over at least the portion of the slot adjacent the liner to restrict entry of air into the cavity. One of the end walls is removable to afford replacement of a depleted supply roll.

18 Claims, 4 Drawing Sheets

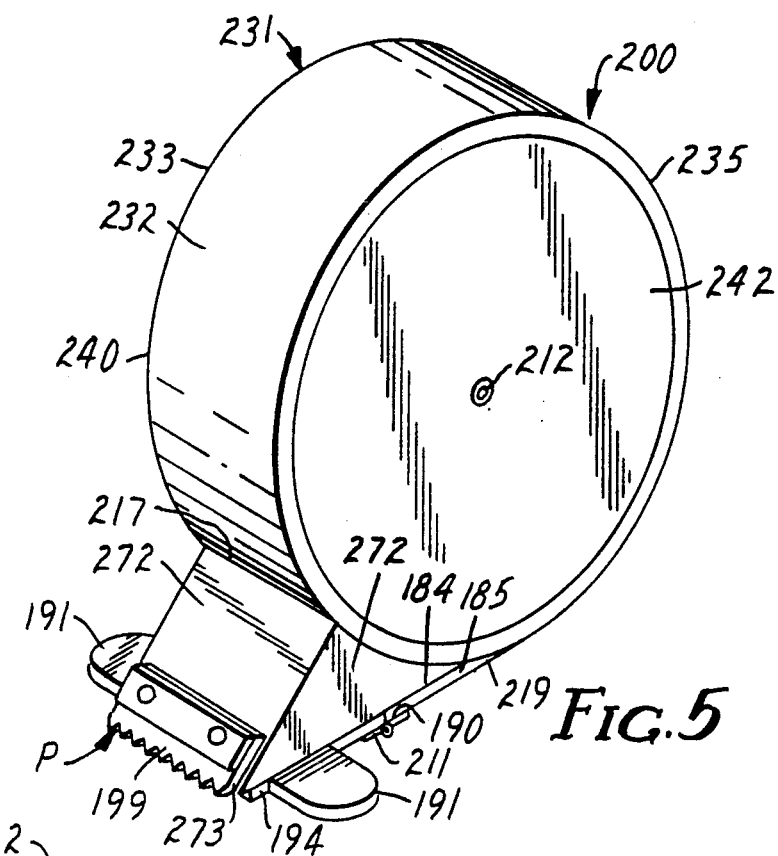
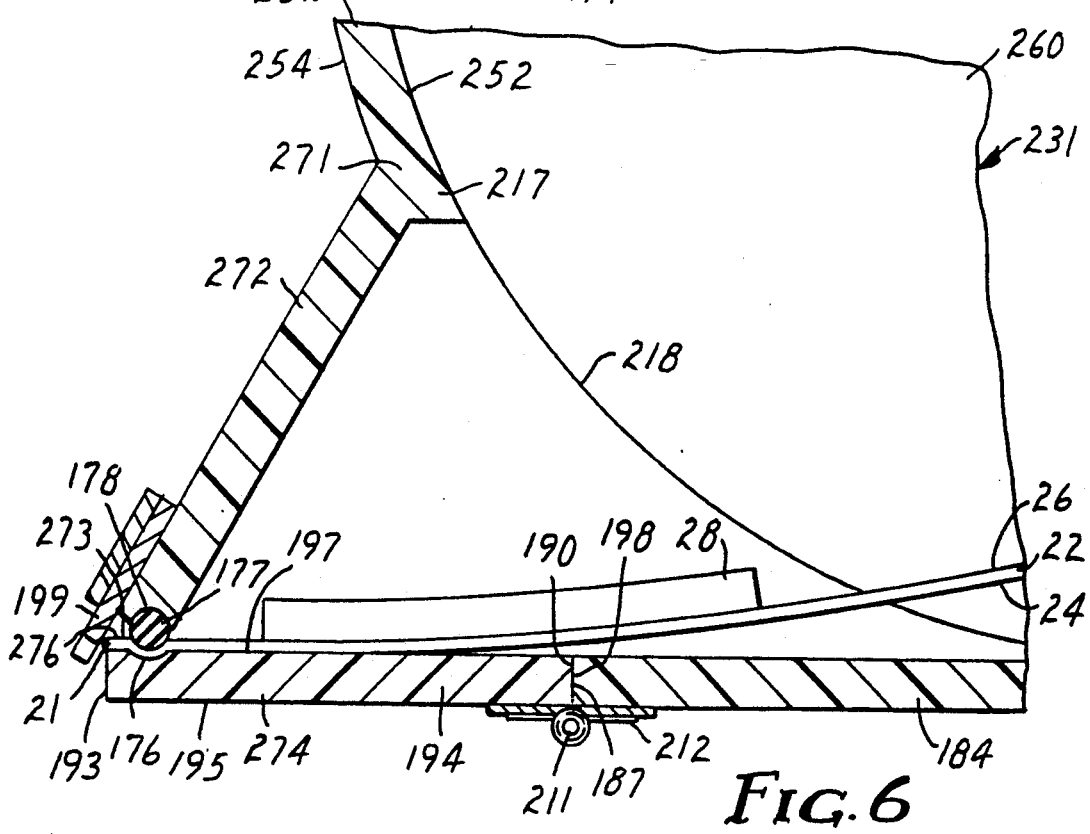

REFILLABLE DISPENSER FOR MOIST ADHESIVE ELECTRODES

TECHNICAL FIELD

The present invention relates generally to a dispenser for a supply roll of medical electrodes.

BACKGROUND ART

A medical instrument used to record electric potentials associated with the electric currents that traverse the heart is an electrocardiograph. To record the electric potentials, the electrocardiograph is connected to the body so that the minute electrical currents produced by the heart during its cycles of contraction can be measured, detected and recorded. The actual interface between the body of a patient and the electrocardiograph consists of several electrodes, such as, disposable electrodes with a moist, conductive adhesive. The moist conductive adhesive electrodes perform the dual function of adhering the electrode to the body of the patient and acting as the electrochemical interface with the body. An example of an electrode of this type and its associated conductive adhesive is disclosed in application U.S. Ser. No. 06/902,396, now U.S. Pat. No. 4,848,353 the entire specification of which is herein incorporated by reference.

Electrodes which utilize moist, conductive adhesives such as the adhesive described in U.S. Pat. No. 4,848,353, are also useful in delivering current to the body, as in transcutaneous electrical nerve stimulation (TENS), and Neuro-Muscular Stimulation (NMS) therapy. Generally, TENS or NMS electrodes are less sensitive to moisture loss than diagnostic electrodes, such as electrodes used in conjunction with an electrocardiograph (i.e. EKG/ECG electrodes).

A significant portion of the cost of conductive adhesive electrodes is due to their air-tight packaging which is critical to their performance, as the electrical function of the electrodes is compromised if they are allowed to dehydrate. Conventionally, electrodes are packaged separately in individual packages (i.e. heat sealed foil pouches), but this packaging is cumbersome for the user and is also relatively expensive.

U.S. Pat. No. 4,584,962 to Cartmel discloses a dispenser of medical electrodes including a supply roll. The leading electrode must pass through a pair of rollers 60 and 62. Once the leading electrode has passed through the rollers 60 and 62, the dispenser does not protect the electrode from dehydration. Thus, the leading electrode tends to dehydrate if it is not used soon after passing through rollers 60 and 62.

DISCLOSURE OF THE INVENTION

The present invention provides a refillable air-restricting dispenser for a supply roll of electrodes which affords bulk packaging of the electrodes and provides protection from dehydration for the leading electrodes on the supply roll.

According to the present invention there is provided the combination of (1) a supply roll comprising an elongate liner wound around a core, a multiplicity of electrodes, and coatings of moist adhesive on the electrodes that releasably adhere the electrodes in spaced relationship along the liner; and (2) an air-restricting dispenser comprising a plurality of walls forming a housing. The walls include a peripheral wall comprising a hollow tubular portion, and first and second opposite end walls, one attached to each end of the peripheral wall. The inner surfaces of the peripheral and end walls define a central cavity within the housing in which the supply roll is positioned, and the peripheral wall has a slot adapted for passage of the liner with electrodes adhered thereto. The dispenser also includes a shield mounted on the housing for movement between an open position spaced from at least a portion of the slot to afford withdrawing the end portion of the liner with the electrodes adhered thereto through the slot, and a closed position over at least the portion of the slot adjacent the liner to restrict entry of air into the cavity.

In a first embodiment of the present invention, the peripheral wall includes a lip portion projecting generally radially outwardly of the tubular portion of the peripheral wall on one side of the slot, and the shield comprises a generally plate-like slightly arcuate member having a generally straight edge surface mounted on the housing for sliding movement between its open and closed positions. In the open position of the shield the straight edge surface is spaced from the lip to afford movement of the liner having electrodes adhered thereto through the slot and in its closed position the straight edge surface abuts the side of the liner opposite the lip.

In a second alternative embodiment of the present invention, the housing has a groove extending around the slot, the walls include a lip similar to the lip of the first embodiment, and the shield is a cup-shaped member having a peripheral surface with a sealing member attached thereto. The shield defines a chamber recessed from the peripheral surface; and the shield is mounted on the housing for pivotal movement between its open position in which the peripheral surface of the cup-shaped member is spaced from the groove so that the liner having the electrodes attached thereto can be withdrawn, and a closed position at which the sealing member is in sealing engagement with the housing groove, and the lip is positioned in the chamber defined by the groove.

According to a third alternative embodiment of the present invention, the hollow tubular portion of the peripheral wall has spaced opposed first and second ends defining a passageway through the tubular portion of the peripheral wall, and the walls forming the housing further include wall portions forming a projecting portion of the housing around the passageway. The projecting portion projects generally radially outwardly from the hollow tubular portion of the peripheral wall, and the wall portions forming the projecting portion of the housing have surfaces defining the slot.

The wall portions forming the projecting portion of the housing include an abutment wall portion included in the peripheral wall and a base wall portion. The abutment wall portion has a first end joined to the first end of the tubular portion of the peripheral wall and the abutment wall portion projects generally radially outwardly from the tubular portion of the peripheral wall. A second distal end of the abutment wall portion is located opposite the first end. The base wall portion is attached to the peripheral wall by being integral therewith. The base wall portion has a first end joined to the second end of the tubular portion of the peripheral wall and the base wall portion projects generally tangentially outwardly from the tubular portion of the peripheral wall. A second distal end of the base wall portion is located opposite the first end. The second distal end of the base wall portion is spaced from the second distal end of the abutment wall portion to define the slot therebetween.

BRIEF DESCRIPTION OF THE DRAWING

The present invention will be further described with reference to the accompanying drawing wherein like reference numerals refer to like parts in the several views, and wherein:

FIG. 5 is a perspective view of a third embodiment of dispenser according to the present invention; and FIG. 6 is a fragmentary cross-sectional view of the dispenser shown in FIG. 5 which is enlarged to show detail.

DETAILED DESCRIPTION

Figure 1:
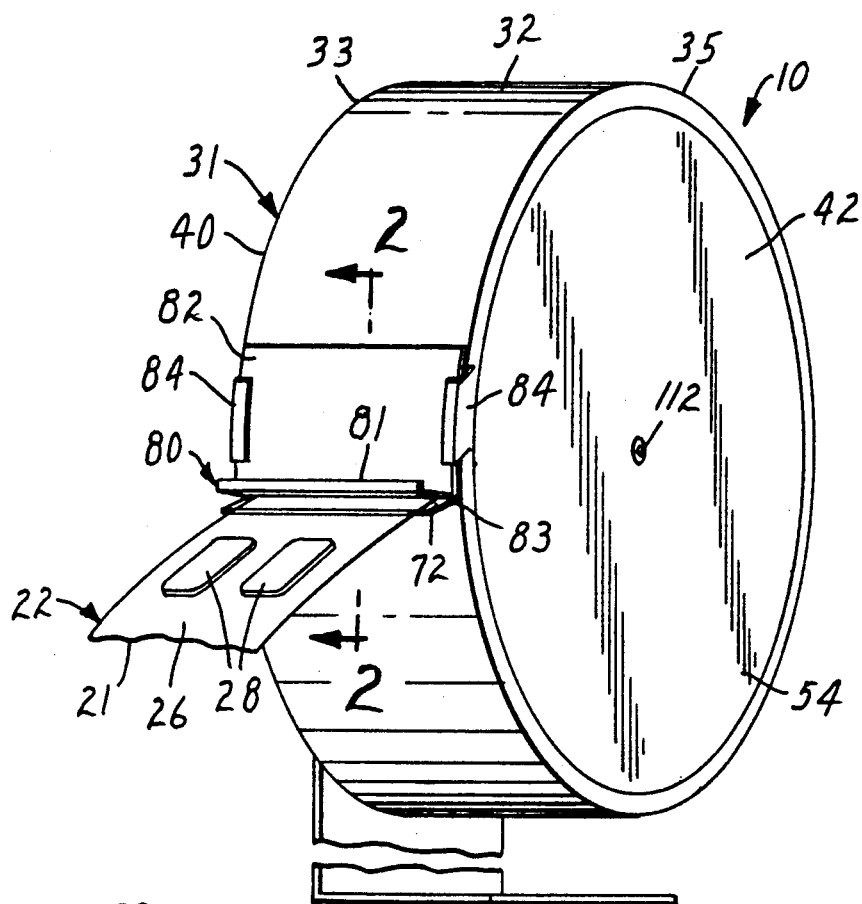
FIG. 1 is a perspective view of a first embodiment of dispenser and supply roll according to the present invention.
Figure 2:
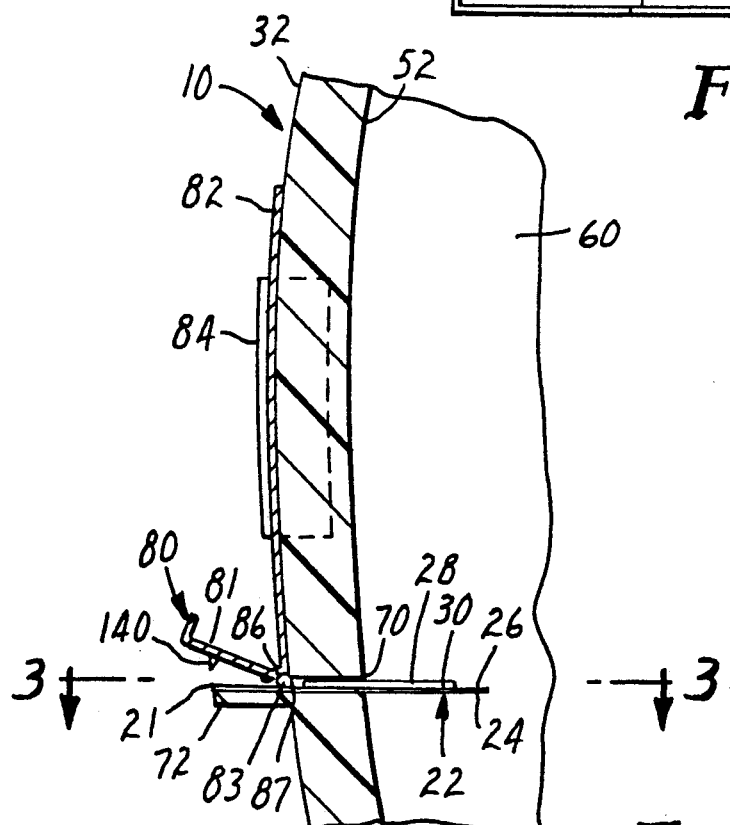
FIG. 2 is an enlarged fragmentary cross-sectional view taken approximately along line 2—2 of FIG. 1.
Figure 3:
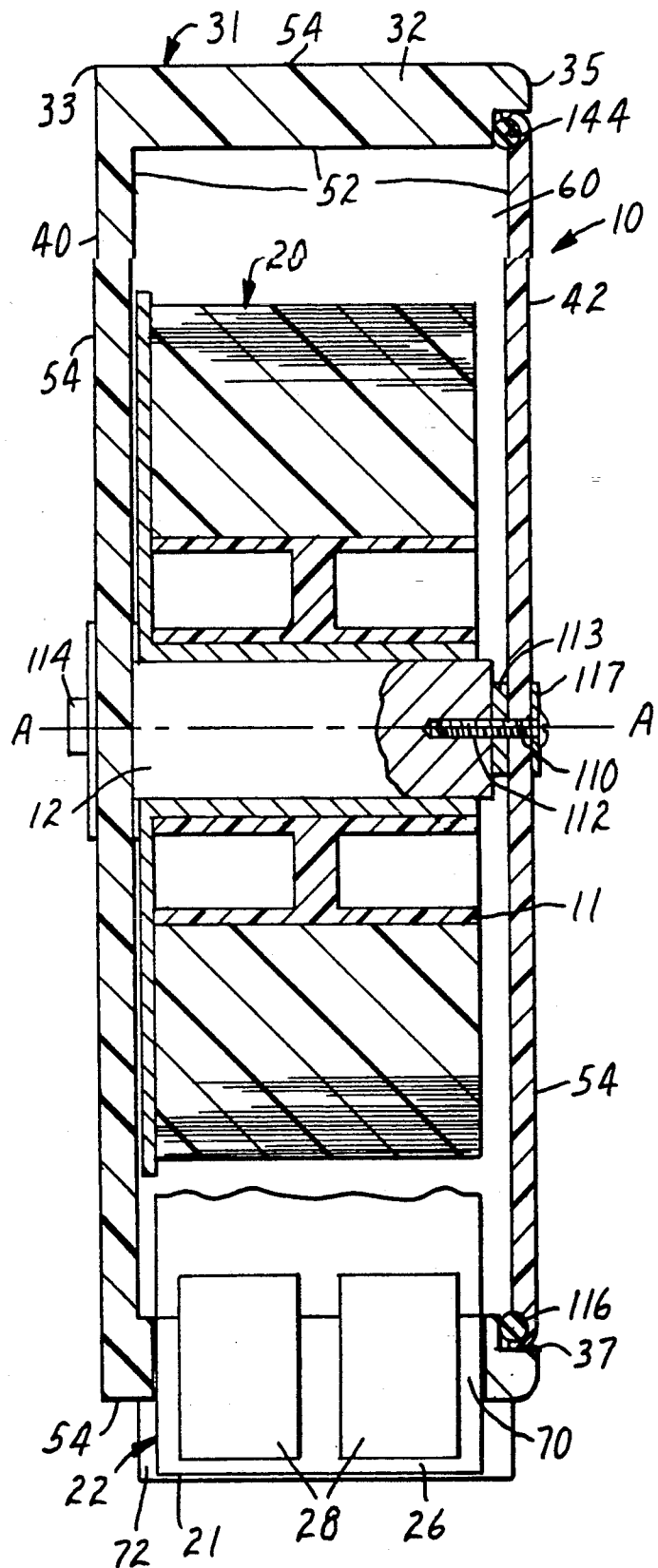
FIG. 3 is an enlarged cross-sectional view taken approximately along line 3—3 of FIG. 2.

Referring now to FIGS. 1 through 3 of the drawings, there is shown a first embodiment of a combination according to the present invention including an air-restricting dispenser 10 and a supply roll 20. The supply roll 20 includes an elongate liner 22 with opposite major surfaces 24 and 26 helically wound around a core 11 (FIG. 3), a multiplicity of electrodes 28, and coatings of moist adhesive 30 on the electrodes which releasably adhere the electrodes 28 in discrete, spaced relationship along surface 26 of the liner 22.

The air-restricting dispenser 10 includes a housing 31 with a plurality of walls including a peripheral wall 32 comprising a hollow tubular portion having an axis A (FIG. 3), and axially spaced ends 33, 35. First and second opposite end walls 40 and 42 are attached to the ends 33, 35 of the peripheral wall 32. The peripheral wall 32 and the first and second opposite end walls 40 and 42 have inner surfaces 52 which define a central cavity 60 within the housing 31. A slot 70 in the peripheral wall 32 communicates between the inner 52 and outer 54 surfaces of the peripheral wall 32 and is adapted to afford passage of the liner 22 with the electrodes 28 adhered thereto. Means including a cylindrical hub 12 journaled between the end walls 40 and 42 (FIG. 3) mounts the supply roll 20 within the cavity 60 for rotation about the axis A with a leading end 21 of the liner 22 extending through the slot 70.

A movable shield 80 is adapted to cover the slot 70 and to restrict air movement through the slot 70. The shield 80 is mounted on the housing 31 for movement between an open position spaced from at least a portion of the slot 70 to afford withdrawing the end portion 21 of the liner 22 with the electrodes 28 adhered thereto through the slot 70, and a closed position with the shield 80 located over at least the portion of the slot 70 adjacent the liner 22 to restrict entry of air into the cavity 60.

The peripheral wall 32 includes a lip portion 72 projecting generally radially outward of the tubular portion of the peripheral wall 32 on one side of the slot 70. The shield 80 comprises a generally plate-like slightly arcuate member 82 having a generally straight edge surface 83. Means such as opposed channels 84 with L-shaped cross sections mount the shield 80 along the outer surface 54 of the housing 31 for sliding movement relative to the housing 31 between an open position with the edge surface 83 spaced from the lip 72 to afford movement of the liner 22 having the electrodes 28 adhered thereto and a closed position (FIG. 2) with the edge surface 83 abutting the surface 26 of the liner 22 opposite the lip 72. Optionally, as shown in FIG. 2, the edge surface 83 may be defined by an edge of a cylindrical sealing member 87 mounted in a groove 86 along an edge of the plate-like member 82, which cylindrical sealing member 87 is comprised of any suitable sealing material such as, but not limited to, Buna-N rubber or an elastomer.

The housing 31 includes means, illustrated in FIG. 3, for affording replacement of a depleted supply roll with a replacement supply roll. The second end wall 42 has a cylindrical hole 110 coaxial with the axis A. The second end wall 42 is separate and removable from the end 35 of the peripheral wall 32 to afford replacement of the supply roll 20 when the liner 22 and the electrodes 28 adhered thereto are depleted. The end 35 of the peripheral wall 32 has recessed L-shaped abutment surfaces 37 which receive the radially outer portion of the second end wall 42. The radially outer portion of the second end wall 42 has an annular groove 144 along its inner surface 52, and an inner sealing member 116 (e.g. an elastomeric O-ring), received in the groove 144. The second end wall 42 is manually movable between a loading position (not shown) with the second end wall 42 spaced from the abutment surfaces 37 to afford removal and replacement of a depleted supply roll and a loaded position (FIG. 3) with the inner sealing member 116 in sealing contact with at least one of the abutment surfaces 37.

In the embodiment shown in FIG. 3, the inner sealing member 116 contacts the axially inner surface of the L-shaped abutment surfaces 37. The axially outer surface of the L-shaped abutment surfaces 37 cooperates with the radially outer portion of the second end wall 42 to provide a labyrinth seal to further protect the electrodes 28 from moisture loss and contamination. Alternatively, the L-shaped abutment surfaces 37 may be omitted and the inner sealing member 116 may directly abut the end 35 of the peripheral wall 32.

A second end wall fastener or screw 112 located within the hole 110 of the second end wall 42 releasably attaches the second end wall 42 to the end of the hub 12 mounting the supply roll 20 within the cavity 60. A sealing means, such as an elastomeric O-ring washer 113, is seated between the end of the hub 12 and the second end wall 42 to provide an air-tight atmosphere in the cavity 60. A sealing washer 117 is positioned between a slotted head of the screw 112 and the wall 42 of the housing 31. Optionally, the screw 112 and hole 110 may be deleted and the second end wall 42 may be snap fit to the L-shaped abutment surfaces 37.

A first end wall mounting means 114 is located on the first end wall 40 and has a projecting portion adapted to mount the housing 31 to a support such as the L-shaped leg L as best seen in FIG. 1. Alternatively, the dispenser 10 may be mounted upon a support using suction cups (not shown). The use of suction cups obviate the need for the mounting means 114.

The outer diameter of the core 11 of the supply roll 20 is selected to afford proper performance of the dispenser 10 as the supply roll 20 becomes nearly depleted. The innermost winding on the helical wind of electrodes 28 has a radius sufficiently large to prevent buckling or "popping off" of the electrodes 28 when the supply of electrodes 28 is depleted to the last few helical windings. For example, for #6860 Electrodes available from the Minnesota Mining and Manufacturing Co. (3M), St. Paul, Minn., which have a length along the liner of 1⅜ 3/8 inches (34 mm), the core diameter should be at least 5 inches (12.5 cm). Generally, the relationship between the outer diameter of the core 11 and the length of an electrode is governed by the equation:

$$D \geq 3.5 X$$

where:

D = the outer diameter of the core 11; and
X = the length of the electrode along the liner.

Dispensers and electrodes which meet the criteria of the above equation prevent bending or buckling of the electrodes 28 when the supply of electrodes 28 is depleted to the last few helical windings.

The dispenser 10 includes cutting means 140 for removing a preselected supply of electrodes 28 from the supply roll 20 which may comprise a serrated edge or a knife edge for example. The cutting means 140 may be seated on the lip 72 or, as shown in FIG. 2, the cutting means 140 may be located on the shield 80. In the embodiment shown in FIGS. 1-3, the cutting means 140 is located on a lip 81 included in the shield 80 and projecting outwardly from the end of the plate-like member 82. A user operates the dispenser 10 by first withdrawing a selected supply of electrodes 28 from the cavity 60, then pushing the plate-like member 82 toward the lip 72 to lock the liner 22 between the edge surface 83 and the lip 72, and then pulling the liner 22 and electrodes 28 upward against the cutting means 140 on the lip 81 of the shield 80 while holding the shield 80 against the remaining portion of the liner 22. Alternatively, in lieu of the cutting means 140, the user may cut the liner with a cutting instrument such as scissors or the liner may be perforated between electrodes.

Figure 4:
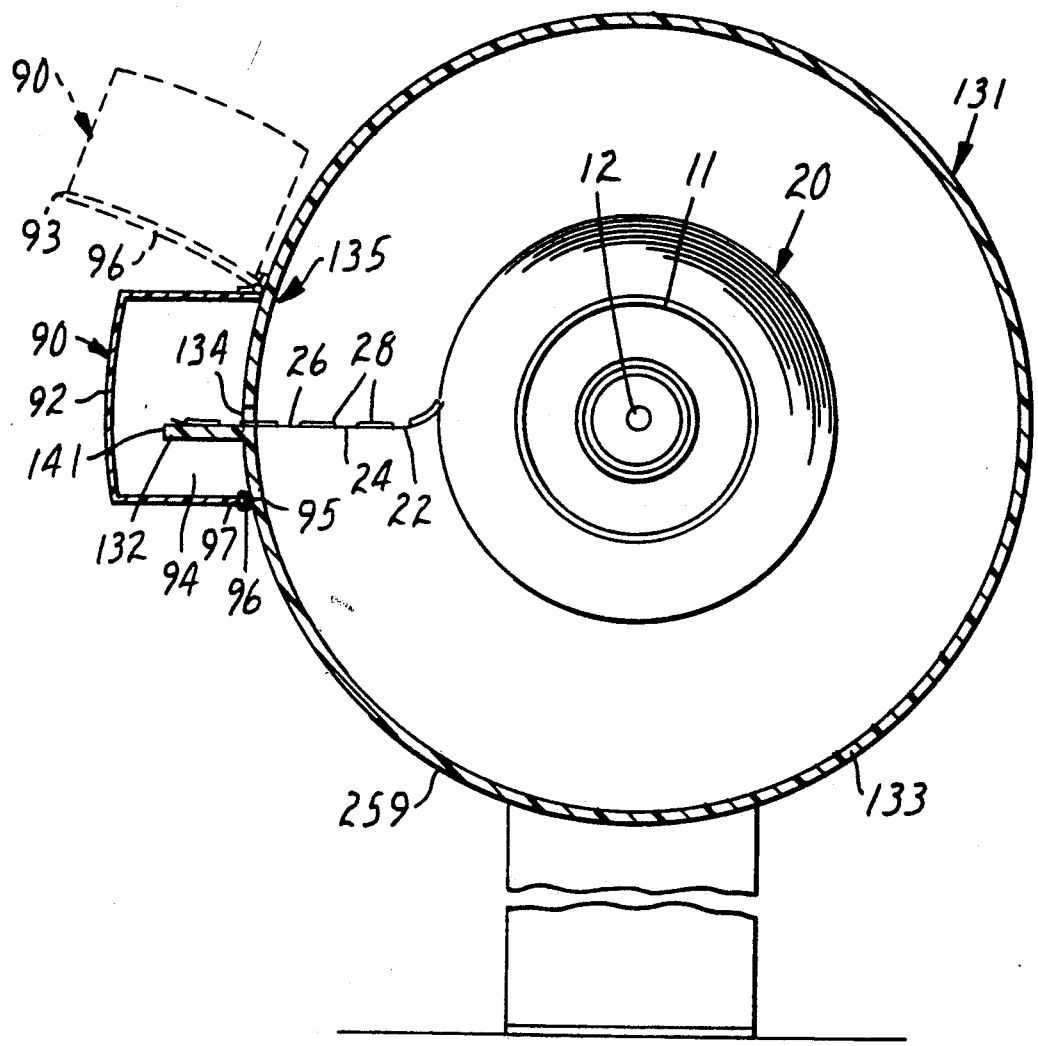
FIG. 4 is a sectional side view of a second embodiment of dispenser according to the present invention.

A second embodiment of a combination according to the present invention is shown in FIG. 4. That combination comprises the supply roll 20 including the electrodes 28 adhered along the liner 22, and wound around the core 11 as described above; and a housing 131. The housing 131 includes a lip portion 132 projecting radially outward of a tubular portion of a peripheral wall 133 of the housing 131 on one side of the slot 134. Also included in the housing 131 is a shield 90 comprising a cup-shaped member 92 having a peripheral surface 93 and defining a chamber 94 recessed from the peripheral surface 93. The peripheral surface 93 has a groove 97 which receives a sealing member 96, for example an elastomeric O-ring. On the peripheral wall 133 of the housing 131, there is a channel 95 which engages the sealing member 96 when the shield 90 is in a closed position (FIG. 4, solid line). Means 135 such as a hinge pivotally mounts the shield 90 on the housing 131 for pivotal movement relative to the housing 131 with the peripheral surface 93 of the cup-shaped member 92 pivotable between an open position (FIG. 4, dashed lines) with the sealing member 96 spaced from the peripheral wall 133 and the closed position (FIG. 4, solid line) with the sealing member 96 in sealing engagement with the channel 95 on the outer surface 259 of the peripheral wall 133.

The embodiment shown in FIG. 4 includes cutting means 141 located on a radially outermost portion of the lip portion 132. The cutting means 141 may comprise any suitable cutting surface, such as, but not limited to a blade or a serrated edge.

FIGS. 5 and 6 illustrate a third embodiment of a combination according to the present invention with the dispenser generally designated by the reference character 200.

Like the combinations described in FIGS. 1 through 4, the combination shown in FIGS. 5 and 6 also comprises the supply roll 20 including the electrodes 28 adhered along the liner 22 and wound around the core 11 as described above, and a housing 231. The housing 231 includes a plurality of walls comprising a hollow tubular peripheral wall portion 232 having an axis defining axial and radial directions, axially spaced ends 233, 235, and first and second opposite end walls 240 and 242 attached to an end 233, 235 of the peripheral wall 232. The peripheral wall 232 and the first and second opposite end walls 240 and 242 have inner 252 and outer 254 surfaces which define a central cavity 260 within the housing 231 (FIG. 6) in which the supply roll 20 is rotatably supported about a hub (not shown). Like the embodiments shown in FIGS. 1-4, the housing 231 is refillable as the end wall 242 is removable to afford replacement of a depleted supply roll.

Unlike the embodiments shown in FIGS. 1 through 4, in the embodiment shown in FIGS. 5 and 6, the hollow tubular portion of the peripheral wall 232 has spaced opposed first 217 and second 219 ends defining a passageway 218 through the tubular portion of the peripheral wall 232, and the walls forming the housing further include wall portions 184, 272 forming a projecting portion P of the housing 231 around the passageway 218. The projecting portion P projects generally radially outwardly from the hollow tubular portion of the peripheral wall 232, and the wall portions 184, 272 forming the projecting portion P of the housing have surfaces 190, 273 defining a slot 274.

The wall portions forming the projecting portion P of the housing include an abutment wall portion 272 included in the peripheral wall 232 and a base wall portion 184. The abutment wall portion 272 has a first end 271 joined to the first end 217 of the tubular portion of the peripheral wall 232 and the abutment wall portion 272 projects generally radially outwardly from the tubular portion of the peripheral wall 232. A second distal end 276 of the abutment wall portion 272 is located opposite the first end 271.

The base wall portion 184 is attached to the peripheral wall 232 by being integral therewith. The base wall portion 184 has a first end 185 joined to the second end 219 of the tubular portion of the peripheral wall 232 and the base wall portion 184 projects generally tangentially outwardly from the tubular portion of the peripheral wall 232. A second distal end 190 of the base wall portion 184 is located opposite the first end 185. The second distal end 190 of the base wall portion 184 is spaced from the second distal end 276 of the abutment wall portion 272 to define the slot 274 therebetween.

Like in the first two embodiments of the present invention, the means mounting the shield 194 on the housing mounts the shield 194 for movement between the open and closed positions. The means mounting the shield 194 on the housing may comprise a hinge 211. The hinge 211 mounts the shield 194 on the base wall 184 for pivotable movement relative to the housing 231 between the open and closed positions. Alternatively the base wall 184 may be omitted with the hinge 211 mounting the shield directly to the second end 219 of the tubular portion of the peripheral wall 232.

The shield 194 illustrated in the embodiment shown in FIGS. 5 and 6 is a generally planar member having first 195 and second 197 major surfaces, and first 198 and second 193 end surfaces. The planar member 194 is pivotally attached along the first end 190 of the base wall portion 184 by means such as a hinge 211 which includes a torsion spring 212. The hinge 211 mounts the shield 194 for pivotal movement between an open position (not shown) with the second major surface 197 spaced from the edge surface 273 of the abutment wall 272 and a closed position (FIG. 6) with the liner 22 secured between the second major surface 197 of the shield 194 and the edge surface 273 of the abutment wall 272. The torsion spring 212 biases the shield 194 toward the closed position.

Along the edge surfaces 273 of the abutment wall 272 are surfaces defining a first U-shaped groove 177. A U-shaped sealing member 178 is seated within the first U-shaped groove 177. The shield 194 also has surfaces defining a second U-shaped groove 176 which corresponds to the first U-shaped groove 177 along the edge surfaces 273. The second U-shaped groove 176 is adapted to receive portions of the U-shaped sealing member 178 and the leading edge 21 of the liner 22 when the shield 194 is in the closed position (FIG. 6).

To operate the dispenser 200 of the embodiment shown in FIGS. 5 and 6, the user initially grasps a handle means 191 for grasping shield 194 without exposing the user to injury from a cutting means 199, such as a blade or a knife. The shield 194 is pivoted to an open position against the bias of the spring 212 to afford removal of a preselected supply of liner 22 and electrodes 28 through the passageway 218 and slot 274. Once a preselected supply of electrodes 28 and liner 22 is withdrawn from the dispenser 200, the shield 194 is released thereby locking the liner 22 between the U-shaped sealing member 178 and the second U-shaped groove 176. The user may then utilize the cutting means 199 mounted on a radially outer surface of the abutment wall portion 272 to remove the preselected supply of liner 22 and electrodes 28. After the supply roll 20 is depleted, the user may replace the supply roll 20 by removing the second end wall 242 by unfastening the releasable second end wall fastener 212, removing the depleted supply roll, placing the replacement supply roll within the central cavity 260 and resealing the second end wall 242 to the housing 231.

The dispenser 200 of the present invention affords moisture loss protection for the leading electrode 28 in the supply roll 20. FIG. 6 shows that the leading electrode 28 rests in the sealed passageway 218 while the dispenser 200 is not in use. To further protect the electrode 28 from moisture loss, the edge surface 187 of the shield 194 and the second distal end surface 190 of the base wall portion 184 are coated with a sealant, such as but not limited to a silicone or rubber gasket material. This feature of the invention prevents unnecessary moisture loss with the leading electrodes on the supply roll 20.

Each of the species disclosed in FIGS. 1-6 includes distinctive features. In the embodiments of FIGS. 1-3 and 5-6, the shield member 80, 194 contacts the liner portion 22 after the leading electrodes 28 are removed. There should be sufficient spacing between electrodes 28 to receive the shield 80, 194 therebetween when the shield 80, 194 is in the closed position. The weight of the shield 80 of the embodiment shown in FIGS. 1 through 3 and the spring 212 of the embodiment shown in FIGS. 5 and 6 hold the liner 22 and electrodes 28 stationary to prevent the leading edge 21 of the liner 22 from accidentally rolling into the cavity 60, 260 of the dispenser 10, 200 when the shield 80, 194 is in the closed position.

The embodiment shown in FIG. 4, however, affords a greater quantity of electrodes 28 per unit length of liner 22 relative to the embodiments shown in FIGS. 1-3 and 5-6, as the cup-shaped member 92 affords closer spacing of the electrodes 28 along the liner 22 because sufficient space between the electrodes 28 for placing the shield 90 is not required.

The present invention has now been described with reference to several embodiments thereof. It will be apparent to those skilled in the art that many changes or additions can be made in the embodiments described without departing from the scope of the present invention. For example, the dispenser 10, 200 may be constructed from any suitable material, such as but not limited to a polymeric material, ABS, polyvinyl chloride and structural foam. Generally, the dispenser is constructed such that it may be sterilized and refillable, but the dispenser may also be constructed such that it is disposable after a single use. Also, the core 11 may be formed of a cylindrical plastic piece shaped with the cross-section shown in FIG. 3 or may comprise a hollow cylindrical cardboard piece. Moreover, the cross-sectional shape of the dispenser is not necessarily circular and may comprise any suitable shape including square and triangular shapes. Thus, the scope of the present invention should not be limited to the structures described in this application, but only by structures described by the language of the claims and the equivalents of those structures.

What is claimed is:

1. In combination, a supply roll comprising
an elongate liner having opposite major surfaces,
a multiplicity of electrodes, and
a coating of moist adhesive on said electrodes,
said adhesive releasably adhering said electrodes in spaced relationship along one of said surfaces of said liner; and
said liner having said electrodes adhered thereto being helically wound to provide said supply roll; and
an air-restricting dispenser comprising:
a plurality of walls forming a housing, said walls including a peripheral wall comprising a hollow tubular portion having an axis, and axially spaced ends; and first and second opposite end walls, one attached to each end of said peripheral wall, said peripheral wall and said end walls having inner and outer surfaces with said inner surfaces defining a central cavity within said housing, said peripheral wall having a slot communicating between said inner and outer surfaces and adapted for passage of said liner having said electrodes adhered thereto;
means mounting said supply roll within said cavity for rotation about said axis with an end portion of said liner extending through said slot; a shield adapted to cover said slot; and means mounting said shield on said housing for movement between an open position spaced from at least a portion of said slot to afford withdrawing the end portion of the liner with the electrodes adhered thereto through the slot, and a closed position over at least the portion of the slot adjacent the liner to restrict entry of air into the cavity.

2. A combination according to claim 1, wherein said peripheral wall includes a lip portion projecting generally radially outwardly of said tubular portion of said peripheral wall on one side of said slot;

said shield comprises a generally plate-like slightly arcuate member having a generally straight edge surface; and said means mounting said shield on said housing mounts said shield for sliding movement relative to said housing between said open position with said generally straight edge surface being spaced from said lip to afford movement of said liner having electrodes adhered thereto and said closed position with said generally straight edge surface in contact with the side of said liner opposite said lip.

3. A combination according to claim 2, wherein said shield has surfaces which define an arcuate groove, and said shield further comprises a generally cylindrical sealing member affixed along said arcuate groove and adapted to restrict entry of air into said cavity when said shield is in said closed position.

4. A combination according to claim 2, wherein said dispenser further comprises cutting means at a radially outer position on said lip, said cutting means being adapted to cut said liner upon manual engagement of said liner with said cutting means.

5. A combination according to claim 1, wherein:

said housing further comprises surfaces defining a channel extending around said slot;

said shield comprises a cup-shaped member having a peripheral surface defining a chamber recessed from said peripheral surface, and having surfaces defining a groove along said peripheral surface; and a sealing member attached to the cup-shaped member within said groove, and said means mounting said shield on said housing mounts said shield for pivotal movement relative to said housing between said open position at which said sealing member attached to said cup-shaped member is spaced from said housing and said closed position at which the sealing member is in sealing engagement with said channel of said housing.

6. A combination according to claim 1, wherein said first end wall is attached to said peripheral wall by being integral therewith, said second end wall is removable from said peripheral wall to afford replacement of said supply roll when the liner and the electrodes adhered thereto have been depleted, and said housing includes means for releasably attaching said second end wall to said peripheral wall.

7. A combination according to claim 6, wherein:

the axially spaced end of said peripheral wall adjacent said second end wall has abutment surfaces defining a recess adapted to receive a radially outer portion of said second opposite end wall, said radially outer portion of said second end wall has surfaces defining an annular groove along the inner surface of said radially outer portion, and said dispenser includes an inner sealing member received in said annular groove and adapted to sealingly engage at least one of said abutment surfaces, and said second end wall is movable between a loading position with the radially outer portion of said second end wall spaced from said abutment surfaces to afford removal and replacement of a depleted supply roll and a loaded position with the inner sealing member in sealing contact with said abutment surfaces of said axially spaced end of said peripheral wall.

8. A combination according to claim 6, wherein said combination further comprises a hole within said second end wall, and said means for releasably attaching said second end wall to said peripheral wall includes a second end wall fastening means located within said hole of said second end wall for sealingly and releasably attaching the second end wall to said means mounting said supply roll within said cavity to facilitate refilling of said dispenser upon depletion of said supply roll.

9. A combination according to claim 1, wherein said hollow tubular portion of said peripheral wall has spaced opposed first and second ends defining a passageway through said tubular portion of said peripheral wall, and said walls forming said housing further include wall portions forming a projecting portion of said housing around said passageway and projecting generally radially outwardly from said hollow tubular portion of said peripheral wall, said wall portions forming said projecting portion of said housing have edge surfaces defining said slot, and said means mounting said shield on said housing mounts said shield on said projecting portion of said housing for movement between said open and closed positions.

10. A combination according to claim 9, wherein said wall portions forming said projecting portion of said housing include:

an abutment wall portion included in said peripheral wall, said abutment wall portion having a first end joined to the first end of said tubular portion of said peripheral wall, projecting generally radially outwardly from said tubular portion of said peripheral wall, and having a second distal end opposite said first end; and a base wall portion included in said peripheral wall, said base wall portion having a first end joined to the second end of said tubular portion of said peripheral wall, projecting generally tangentially outwardly from said tubular portion of said peripheral wall, and having a second distal end opposite said first end;

the second distal end of said base wall portion being spaced from the second distal end of said abutment wall portion to define said slot therebetween; and said means mounting said shield on said housing mounts said shield on said base wall for pivotable movement relative to said housing between said open and closed positions.

11. A combination according to claim 10, wherein said peripheral surface of said abutment wall portion includes surfaces defining a first U-shaped groove; and said dispenser further comprises a U-shaped sealing member affixed to said first U-shaped groove of said abutment wall portion.

12. A combination according to claim 11, wherein said shield further includes surfaces defining a second U-shaped groove adapted to at least partially engage said U-shaped sealing member when said base wall portion is in said closed position.

13. A combination according to claim 9, wherein said means mounting said shield on said housing comprises a spring loaded hinge adapted to bias said shield toward said closed position, and said housing has cutting means located on a radially outer portion thereof.

14. A combination according to claim 9, wherein said shield has a sealant material coated on an edge surface thereof.

15. A combination according to claim 1, wherein said means mounting said supply roll within said cavity for rotation about said axis comprises a hub means having an outer surface with an outer diameter.

16. A combination according to claim 15, wherein said combination further comprises said liner having said electrodes adhered thereto being helically wound about a core having inner and outer surfaces defining inner and outer diameters with the inner surface of said core being journaled on the outer surface of said hub means and wherein said combination satisfies the equation:

$$D \geq 3.5 X$$

where:
- $D$ = the outer diameter of the core; and
- $X$ = the length of the electrode along the liner.

17. A combination according to claim 15, wherein said outer diameter of said hub means is at least five inches (12.5 centimeters).

18. A combination according to claim 1, wherein said liner has perforations registered between electrodes.

* * * * *

UNITED STATES PATENT AND TRADEMARK OFFICE
CERTIFICATE OF CORRECTION

PATENT NO. : 5,154,335
DATED : October 13, 1992
INVENTOR(S) : Timothy S. Bredow and David L. Robbins It is certified that error appears in the above-indentified patent and that said Letters Patent is hereby corrected as shown below:

Col. 5, line 12, "$\geq$" should read --$>$--.
Col. 12, line 5, "$\geq$" should read --$>$--.

Signed and Sealed this

Nineteenth Day of July, 1994

Attest:

BRUCE LEHMAN

*Attesting Officer*   *Commissioner of Patents and Trademarks*